(12) United States Patent
Subert

(10) Patent No.: US 8,448,492 B2
(45) Date of Patent: May 28, 2013

(54) METHOD FOR IN-SITU DETERMINING THE COMPACTNESS OF GRAINY MATERIAL LAYERS AND DEVICE FOR PERFORMING THE PROCESS

(76) Inventor: Istvan Subert, Erd (HU)

( * ) Notice: Subject to any disclaimer, the term of this patent is extended or adjusted under 35 U.S.C. 154(b) by 0 days.

(21) Appl. No.: 12/867,886

(22) PCT Filed: Jul. 17, 2009

(86) PCT No.: PCT/HU2009/000059
§ 371 (c)(1),
(2), (4) Date: Aug. 17, 2010

(87) PCT Pub. No.: WO2010/007454
PCT Pub. Date: Jan. 21, 2010

(65) Prior Publication Data
US 2011/0146376 A1  Jun. 23, 2011

(30) Foreign Application Priority Data

Jul. 17, 2008 (HU) .................................... 0800441

(51) Int. Cl.
*G01N 3/00* (2006.01)
(52) U.S. Cl.
USPC ..................................................... 73/12.06
(58) Field of Classification Search
USPC ............................................. 73/12.6, 12.06
See application file for complete search history.

(56) References Cited

U.S. PATENT DOCUMENTS

| 5,390,535 | A | * | 2/1995 | Smock et al. ..................... 73/79 |
| 5,457,984 | A | * | 10/1995 | Ambur et al. ................. 73/12.09 |
| 5,841,019 | A | * | 11/1998 | Drabrin et al. ............... 73/12.11 |
| 5,983,702 | A | * | 11/1999 | Ahn et al. ..................... 73/12.06 |
| 6,050,127 | A | * | 4/2000 | Rao et al. ..................... 73/12.13 |
| 6,536,263 | B1 | * | 3/2003 | Wood et al. ....................... 73/82 |
| 6,925,858 | B2 | * | 8/2005 | Miles et al. ....................... 73/84 |
| 7,617,718 | B2 | * | 11/2009 | Kinast et al. ..................... 73/84 |

FOREIGN PATENT DOCUMENTS

| DE | 10036310 | 2/2002 |
| DE | 10036310 A1 * | 2/2002 |
| GB | G82249181 | 4/1992 |

* cited by examiner

*Primary Examiner* — Lisa Caputo
*Assistant Examiner* — Jamel Williams
(74) *Attorney, Agent, or Firm* — Mark M. Friedman

(57) ABSTRACT

The object of the invention is a device for in-situ determining the compactness of grainy material layers, especially determining the compactness of material layers containing equally solid part, liquid and gaseous phases e.g. soils, that consists of a guide body, a loading disc connected with the guide body and a dropping-weight movable relating the loading disc along the guide body. The characteristic feature of the device is that an indicator figure (20) is adjusted to a dropping weight (13), the indicator figure (20) has a guide organ (21), wherein one of the guide organs (21) and the guide body (11) are at least periodically in a connection with each other restricting the direction of movement and the guide body (11) is complemented with a length measuring unit (30).

6 Claims, 1 Drawing Sheet

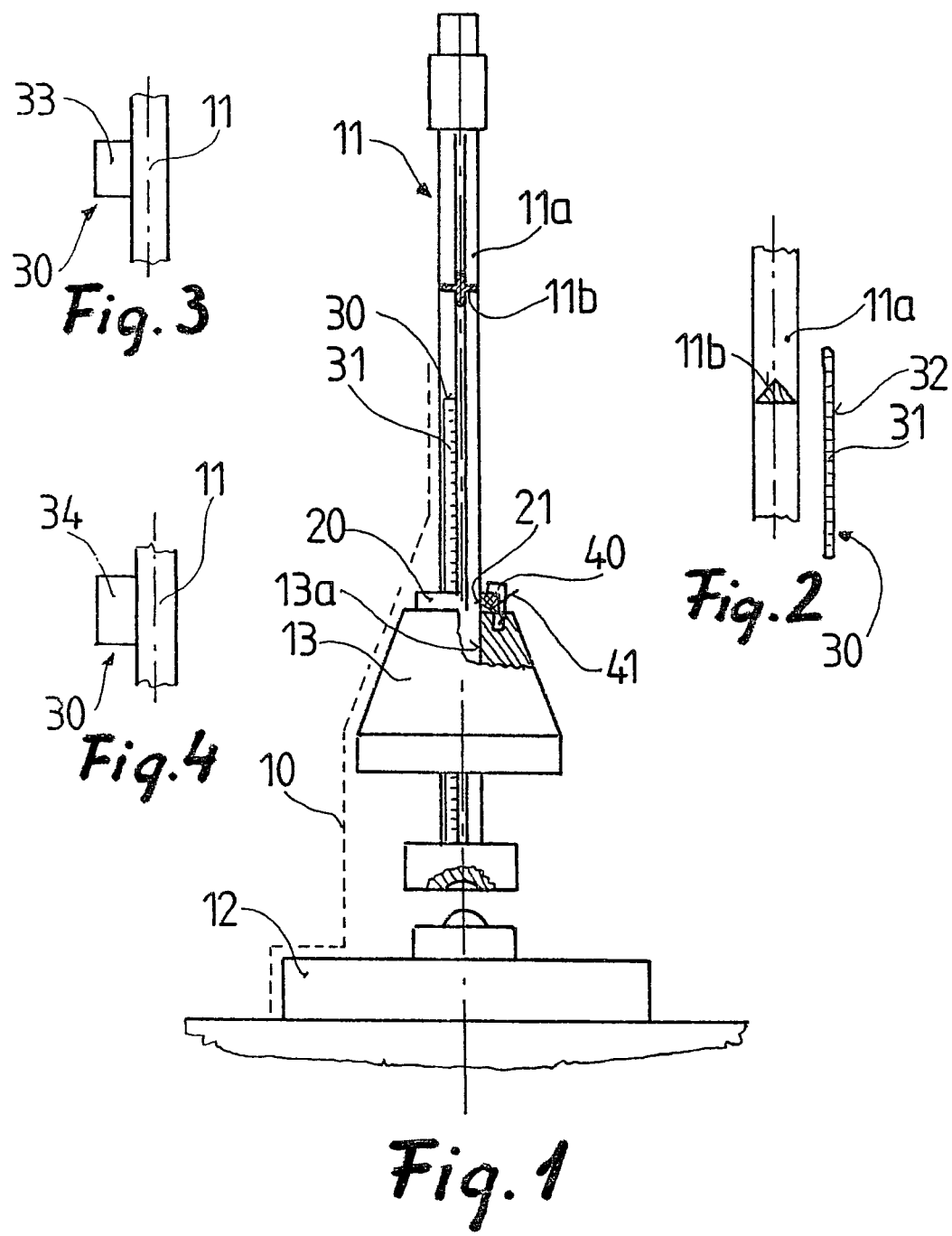

METHOD FOR IN-SITU DETERMINING THE COMPACTNESS OF GRAINY MATERIAL LAYERS AND DEVICE FOR PERFORMING THE PROCESS

This patent application is a National Phase Application of PCT/HU2009/000059 filed on Jul. 17, 2009, which claims priority of HU 08 00441 filed Jul. 17, 2008.

The object of the invention is a device for in-situ determining the compactness of grainy material layers, especially determining the compactness of material layers containing equally solid part, liquid and gaseous phases e.g. soils, that consists of a guide body, a loading disc connected with the guide body and a dropping-weight movable relating the loading disc along the guide body.

Furthermore, the object of the invention is also a method for in-situ determining the compactness of grainy material layers, especially determining the compactness of material layers containing equally solid part, liquid and gaseous phases e.g. soils, using a device consisting of a loading disc connected with a guide body and a dropping-weight movable relating the loading disc along the guide body, as measuring tool. The loading disc is placed on the surface of the material layer to be examined, then with the help of the dropping weight deforming impact energy of given value is transmitted to the loading disc, and following it the compactness of the material layer is determined.

Equipment with dropping weights has been applied for geotechnical measurements for a long time already. Among others, equipment with a heavy dropping weight can be learned from the patent description GB 2.249.181. However it has the disadvantage that because of the big size and mass of the equipment transporting, moving and applying it on the spot is awkward.

For elimination of this deficiency devices with light dropping weights were developed, that lately are winning an increasing area worldwide, both in in-situ geotechnical measurements and in soil laboratories. The essence of this solution is that a weight of given mass drops and strikes at the disc laying on the soil to be examined. Due to the dynamic force effect the disc sinks but also throws back the loading mass. Thus on the one hand, the disc compacts the soil under it, on the other hand, it recoils according to the law of impulse. Depending upon the volumetric composition of grainy-water-air part of the soil i.e. the compaction characterized by it, the soil is compressed, consuming a small part of the energy, causing deformation that generally can be measured directly. E.g. the No DE 100 36 310 publication document concerns a device with light dropping weight.

The key question of designing the measuring device i.e. the method for the accurate and reliable determination of the compaction, is the deformation under the disc. The measurement can be performed using the most variable methods, but the application of acceleration gauges is prevailing. In such a way, from the information on acceleration due to gravity at the given degree of latitude, the acceleration, and from it the sinking of the disc is determined, in the knowledge of the time, measured with microsecond accuracy.

However, a disadvantage of the applied methods is that under the disc a very small deformation during a very short time, and time interval shall be measured.

It can be classified a disadvantage that for the accurate determination of the examined physical soil parameters the time shall be measured with microsecond accuracy that requires very costly structural elements, thus increasing also the cost of the device.

It is also a disadvantage that electronic tools shall be placed in the loading disc of the device and they shall be provided also with proper voltage supply.

It can be also mentioned as a disadvantage that the probability of failures of electronic parts exposed to continuous dynamic force effects is high. With devices working in a wrong way accurate measurements cannot be performed, and that may cause numerous further mistakes.

The aim of the solution of the invention was to eliminate the deficiencies of known devices and to create an option with which the compaction of the subsoil can be determined in a substantially simpler way but with the required accuracy so that measuring microsecond time intervals is not needed, and the disc leaning on the soil can be made independent on the measuring method.

In connection with this, the goal of the invented method was to develop a simple solution easily usable, independent from the possible failures of electronic tools and their electric energy supply, still providing the result of required accuracy for the determination of physical soil parameters.

The base of the invention's idea was that the height of recoiling is notoriously a very sensitive characteristic of the subsoil compaction under the effect of dropping. In the case of a bed with small deformation recoiling of the dropping weight is higher, while in case of higher deformation recoiling is much lower. The "elastic modulus" of the soil characterizes the compression. On this base, with masses that can be considered constant, in the function of the soil elastic modulus, the deformation can be determined from recoiling. As the stress distribution and deformation spreading in the soil can be calculated according to the Boussinesq-theory, and in the same time, the disc diameter of the measuring tool, the mass of the dropping weight and the dropping height are constant, the relation can be determined with mathematic method, thus the deformation under the disc can be estimated. The maximal elevation of the recoiling dropping weight after the dropping and collision is $h=v^2/2g$, i.e. it is determined only by the acceleration of gravity and the velocity resulted by the recoiling impulse. In such a way, from the maximal elevation itself it can be estimated the back throwing "spring force", the soil elastic modulus in this case, that can be recalculated for deformation with the Boussinesq formula, in the knowledge of the "$c=\pi/2$" Boussinesq disc factor and $\mu$ Poisson's ratio or cross contraction factor. On the base of the above, the degree of the recoiling of the dropping weight placed on the loading device can be brought into an unambiguous relationship with the deformation under another part, the loading disc i.e. the "springing" characteristic because of it. In case of such relationship there exists a possibility for measuring it and calculating the elastic characteristics of the soil. Contrary to those applied in known solutions, the compaction of the soil does not have to be determined, instead the magnitude of the dropping weight recoiling shall be established. Namely, its measurement is substantially simpler.

Thus the design of the invented device was resulted by the perception that connecting a structural element with the dropping weight moving together with it during a given time interval of the measurement but becoming independent of it in a proper moment, thus it is able to indicate the degree of dropping weight recoiling i.e. its maximal elevation for a longer period of time, so this measurement of length can be performed with high accuracy and simple tools, not depending on time, and in such a way the task can be solved.

The perception leading to the invented method was that the value of dropping weight recoiling can be simply measured if to indicate the value of recoiling with the help of a properly selected indicator figure, and from this measuring figure accurate data can be determined concerning the required physical soil characteristics.

According to the appointed goal, the invented device for in-situ determining the compactness of grainy material layers, especially for determining the compactness of material layers e.g. soils containing equally solid part, liquid and gaseous phase, consisting of a guide body, loading disc connected with it and a dropping weight movable relating the loading disc along the guide body, is designed in such a way that an indicator figure is adjusted to the dropping weight, the figure having a guide organ connected at least periodically with the guide body restricting the direction of moving and the guide body is complemented with a length measuring unit.

A further criterion of the invented device may be that a fixing unit having a releasing mechanism is adjusted between the dropping weight and the indicator figure, and the indicator figure is fastened to the dropping weight by the fixing unit on a part of the motion trajectory.

In a possible option of the device, the length measuring unit has an ordered pitch sequence, the ordered pitch sequence is situated on the surface of the guide body or the length measuring unit has a measuring staff provided with a pitch sequence, and the measuring staff is situated on the guide body and can be removed from it.

With another option of the invention, the length measuring unit has an optical or ultrasonic sensor that can be fastened to the guide body.

In other variants of the device the guide body has an elongated bar, and the bar has an other guide organ of triangular, quadrangular or multiangular cross section.

According to the appointed goal, the invented method for in-situ determining the compactness of grainy material layers, especially determining the compactness of material layers containing equally solid part, liquid and gaseous phases e.g. soils,—in the course of which a device consisting of a loading disc connected with a guide body and a dropping weight movable relating the loading disc along the guide body is used as a measuring tool, the loading disc is placed on the surface of the material layer to be examined, then with the help of the dropping weight deforming impact energy of given value is transmitted to the loading disc, and following it the compactness of the material layer is determined,—rests on the principle that before transmitting the deforming impact energy to the loading disc the dropping weight is associated with an indicator figure, then after transmitting the deforming impact energy to the loading disc the value of dropping weight recoiling from the loading disc is determined with the help of the indicator figure, and the compactness of the material layer under the loading disc is established on the base of the recoiling value.

A further criterion of the invented method may be that for determining the compactness of the material layer we use a data base resting on the established relationship between deformation and compactness degree.

An advantage of the invention is that contrary to usual solutions, due to the dropping weight complemented with the special indicator figure, the complicated up to now determination of soil mechanics characteristics can be reduced to a distance measurement performable easily.

A further advantage resulted by the above is that the device of simple design does not require placing electronic elements important in the course of measurement into the loading disc and their voltage supply either reading of values measured electronically, thus the invented device has substantially simpler design and operation and minimal failure probability. It is also a technical advantage that the design of the loading disc can be greatly reduced because the actual measurement is performed not there.

It can be considered an advantage that the measuring scope of the invented device is more advantageous, its reachable accuracy is higher and even the application of newer length measuring techniques e.g. optoelectronics, ultrasonic distance measuring etc. becomes possible.

It is also an advantage that with the application of the device the high accuracy time measurements can be avoided and the loading disc can be made independent from the measuring method. In this case also various disc diameters can be used very cheaply that substantially extends the application in quality and scientific sense.

It shall be underscored as an important measuring technical advantage that when using the invented device it is all the same at what latitude the measurement is performed as the effect of acceleration of gravity is wiped out in the course of drop-recoil difference calculation, thus it does not have to be considered in calculations. Reading of recoiling height can be immediately converted into loading disc sinking. It can also be considered an advantage of this type that the dropping weight recoiling is much higher than the loading disc sinking, so the reading of recoiling does not require such a high accuracy as the same result can be reached with lower measuring accuracy.

A further advantage of the device is that failures are more avoidable, costs and prices of collateral measuring instruments can be decreased. Because of these, the spreading and technical usefulness can increase.

A great advantage resulted by the above is that the device can be advantageously used under more difficult geographical and weather conditions, in given cases on uninhabited territories, for military uses and in cases of long and continuous measuring requirements, as with its proper design measurements do not require any energy supply, batteries, electricity. Thus measuring devices with light dropping weights and such reading systems—because of their more advantageous costs, simple operation and low failure probability— can be applied in developing or undeveloped countries substantially easier.

Further we describe the invented device in more details, in connection with a working example, on the base of its drawing. On the drawing:

FIG. 1.—View of a device option, partly in section,

FIG. 2.—Demonstration detail of the length measuring unit of the device,

FIG. 3.—Demonstration detail of another option of the length measuring unit of the device, FIG. 4.—Demonstration detail of still another option of the length measuring unit of the device.

On FIG. 1. a possible variant of the invented device 10 is shown. It may be observed that the device 10 consists of the loading disc 12 resting on the soil to be measured, the guide body 11 fitting to loading disc 12 in a way allowing the transmission of the load, the dropping weight 13 and indicator figure 20 movable on the guide body 11.

Guide body 11 is expediently a bar 11a of a cross section for serving as another guide organ for the dropping weight 13 and indicator figure 20. With the present design the guide body 11 has a bar 11a of cross section of cross form. Essentially this cross form constitutes the other guide organ 11b.

Naturally, the opening 13a of dropping weight 13 is adjusted to the other guide organ 11b form of bar 11a on the guide body 11. Dropping weight 13 is made from a heavy material, expediently a metal.

A guide organ 21 of indicator figure 20 is fitted also to the other guide organ 11b that in this design is also a cross form opening. Indicator figure 20 itself is a thin metal e.g. aluminum disc of very small mass.

In this variant of the invention, the indicator figure 20 has a fastening unit 40 provided with a releasing mechanism 41. The task of the fastening unit 40 is to assure the joint movement of indicator figure 20 and dropping weight 13 during a given period of the measurement, while the releasing mechanism is responsible for cutting the connection between the indicator figure 20 and the dropping weight 13 in the moment of connection between the loading disc 12 and the dropping weight 13. Another task of the fastening unit 40 is to allow closing together the indicator figure 20 and guide body 11 free of 11a bar dislocation.

Device 10 has still a length measuring unit 30 that in the present variant is a pitch sequence 31 engraved on the bar 11a. The pitch sequence 31 that is here an accurate mm scale allows the accurate reading of the elevation of indicator figure 20. However it shall be noted that the pitch sequence 31 of the length measuring unit 30 can be not only a mm scale but also scales of ordered indications directly proportional to the sinking of loading disc 12, essentially giving its value. Consequently, with the length measuring unit 30 can be measured not only the length of indicator figure 20 elevation, but in case of properly determined proportion the given pitch sequence 31 can show physical parameters different from length that has a given correlation with the elevation of indicator figure 20.

FIG. 2. shows another design of the length measuring unit 30. It can be seen that here the length measuring unit 30 is a pitch sequence 31 engraved on a measuring staff 32 that is not a part of the bar 11a of the guide body 11, but in the course of using the device can be set on the dropping body 13 as a base surface for easy determination of the maximal elevation of the indicator figure 20. Here it shall also be noted that the bar 11a of the guide body 11 has a regular triangular cross section. This cross section form constitutes the other guide organ 11b of the guide body 11.

On FIG. 3. a length measuring unit 30 fastened on the guide body 11 can be seen that contains an optical sensor 33, in this case a laser rangefinder, while on FIG. 4. the length measuring unit 30 fastened on the guide body 11 is an ultrasonic rangefinder 34. It shall be noted here that the length measuring unit 30 can be any mechanical, optical or other measuring tool suitable for determining the distance relating a reference level with 0.1 mm accuracy, e.g. indicating it or making it definable.

When using the invented device 10, we adjust the fastener unit 40 of the indicator figure 20 in such a way that it connects the indicator figure 20 with the dropping weight 13 for joint movement. Following it, lifting the dropping weight 13 on the bar 11a of the guide body 11 to a prescribed height, then releasing the dropping weight 13, the operation of the device 10 starts. Due to the joint operation of the opening 13a of the dropping weight 13 and of the other guide organ 11b of the bar 11a, the dropping weight 13 accelerating along length direction of the bar 11a falls on the loading disc 12. Arriving on the loading disc 12, the dropping weight 13 suddenly stops, in consequence the releasing mechanism 41 of the fastener unit 40 starts operation, the closing joint with the form provided by the fastener unit 40 ceases and the indicator figure 20 becomes separable from the dropping weight 13. In consequence of the collision of dropping weight 13 and loading disc 12 not only the releasing mechanism 41 starts, but the dropping weight 13—according to the law of conservation of momentum—also recoils from the loading disc 12. The elevating dropping weight 13 now pushes the indicator figure 20 before itself during the whole period of the elevation of dropping weight 13. However, when the elevation of dropping weight 13 ceases, the operation of the fastener unit starts again and at this highest point of elevation the indicator figure 20 closes with the bar 11a. The fixed position of the indicator figure 20, thus the elevation height is readable with the help of the pitch sequence 31 of the length measuring unit 30 on the bar 11a.

For performing the next measurement, indicator figure 20 shall be released and moving it on the bar 11a to the dropping weight 13 joined again with it, the process described previously can be repeated.

It can be understood that the operation of the device 10 is identical in every aspect not depending upon the operating principle of the length measuring unit 30. The length measuring unit 30 determines only the way of establishing the maximal elevation height.

In the following, we are describing examples of the invented method in details.

EXAMPLE 1

We determined the maximal recoiling of the dropping weight 13 of the device 10 by reading the maximal recoiling visually, afterward. The measurement itself was performed in a way that can be learned from patent description No HU . . . with the difference that we measured and used the recoiling of the dropping weight 13 instead of the soil compaction. In the course of the process, we lifted dropping weight 13 on the prescribed height and released it from there. The freed dropping weight 13 fell on the loading disc 12 then recoiling from it lifted indicator figure 20 that stopped at the maximal recoiling. Then we determined and recorded the fixed position of the indicator figure 20 from the pitch sequence 31 of the length measuring unit 30. We released the dropping weight 13 several times on the same place and recorded the results in every case.

We included the degree of recoiling in a table, then in case of measurement series, following each dropping, calculated the differences between measured recoiling maximums. In the next column of the table we summed, added and weighted these values, then introduced the resulted values in a diagram. Joining the points with a line, at an assigned abscissa (17000) we got the section ($\xi$) proportional to the value of deformation index Dm given in CEN WA15468. From it the relative dynamic degree of compactness Trd %=100−3.65*Dm could already be easily determined.

In the end of measurement series we experienced that the recoiling height of the dropping weight 13 was inversely proportional to the deformation of the subsoil, while the difference between multiple readings depended on the difference between deformations of the subsoil logarithmically. The previous (absolute) value is the dynamic elastic modulus (elasticity), the latter was suitable for the determination of the dynamic degree of compactness (compaction).

Filling out the nomogram annexed to device 10 but not described here, we calculated the dynamic compactness degree with simple hand methods, on the spot of the measurement.

The invented device and the method performable with it can be simply applied in all areas where physical soil parameters are to be determined under disadvantageous conditions, in a quick, simple and accurate way.

LIST OF REFERENCE SYMBOLS 10 device 11 guide body
11a bar 11b other guide organ
12 loading disc
13 dropping-weight
13a opening
20 indicator figure
21 one of the guide organs
30 length measuring unit
31 pitch sequence
32 measuring staff
33 optical sensor
34 ultrasonic sensor
40 fastening unit
41 releasing mechanism

The invention claimed is:

1. Device for in-situ determining the compactness of grainy material layers, especially determining the compactness of material layers containing equally solid part, liquid and gaseous phases, that consists of a guide body, a loading disc connected with the guide body and a dropping weight movable relating the loading disc along the guide body, said device characterized by that an indicator figure (20) is adjusted to a dropping weight (13), the indicator figure (20) has a guide organ (21), wherein one of the guide organs (21) and the guide body (11) are at least periodically in a connection with each other restricting the direction of movement and the guide body (11) is complemented with a length measuring unit (30), wherein the guide body (11) has an elongated bar (Ha) and the bar (Ha) has another guide organ (1 ib) of triangular, quadrangular or multiangular cross section.

2. Device as set forth in claim 1, wherein between the dropping weight (13) and the indicator figure (20) a fastener unit (40) provided with a releasing mechanism (41) is introduced and the indicator figure (20) is fastened to the dropping weight (13) on a part of the movement trajectory with the help of the fastener unit (40).

3. Device as set forth in claim 1, wherein the length measuring unit (30) has an ordered pitch sequence (31) and this ordered pitch sequence (31) is situated on the surface of the guide body (11).

4. Device as set forth in claim 1 wherein the length measuring unit (30) has a measuring staff (32) provided with a pitch sequence (31) and the measuring staff (32) is adjusted to the guide body (11) in a removable way.

5. Device as set forth in claim 1, wherein the length measuring unit (30) has optical sensor (33) that can be fastened on the guide body (11).

6. Device as set forth in claim 1 wherein the length measuring unit (30) has a sensor (34) that can be fastened on the guide body (11).

* * * * *